United States Patent [19]

Bennett

[11] 4,419,098
[45] Dec. 6, 1983

[54] NEEDLE SHIELD

[75] Inventor: Michael C. Bennett, Summit, N.J.

[73] Assignee: Becton Dickinson and Company, Paramus, N.J.

[21] Appl. No.: 320,361

[22] Filed: Nov. 12, 1981

[51] Int. Cl.³ ............................................... A61M 5/00
[52] U.S. Cl. ................................................ 604/263
[58] Field of Search .................... 128/215, 216, 218 R, 128/218 S, 218 N, 221

[56] References Cited

U.S. PATENT DOCUMENTS

| | | | |
|---|---|---|---|
| 3,381,813 | 5/1968 | Coanda et al. | 128/218 S X |
| 3,469,581 | 9/1969 | Burke | 128/218 N X |
| 3,721,241 | 3/1973 | Klohr et al. | 128/221 |
| 4,240,425 | 12/1980 | Akhavi | 128/218 N |

FOREIGN PATENT DOCUMENTS 2622515 12/1976 Fed. Rep. of Germany ... 128/218 N

Primary Examiner—John D. Yasko

[57] ABSTRACT

A needle shield is provided for a needle holding assembly, such as a blood collection assembly, which reduces the possibility of contamination to the user by providing a radially positioned guidance groove at the entry of the shield for easy guidance of the used needle point back into the shield.

4 Claims, 1 Drawing Figure

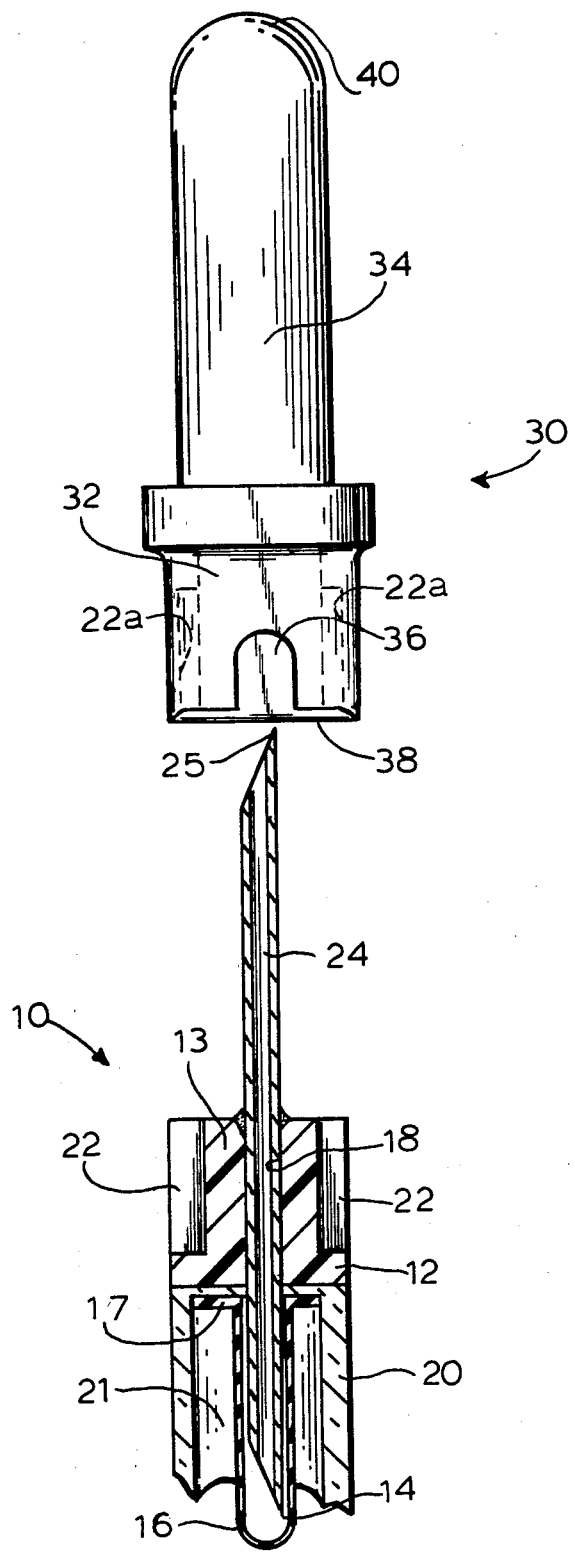

NEEDLE SHIELD

BACKGROUND AND STATEMENT OF THE INVENTION

Generally speaking, this invention relates to a needle holder assembly. More particularly, this invention relates to an arrangement of protective needle shield for such an assembly, and particularly for a liquid handling assembly in medical applications. As will be appreciated, when a blood collection assembly, for example, is to be used, it is necessary to expose the needle for such use. Prior to the use, however, the needle is protected from contamination by a needle shield which extends over the entire length of the needle and has cooperating grooves for fitting over and gripping the needle holder. Generally, the arrangement includes a plurality of circumferentially spaced grooves internally of the needle shield at the entry opening portion thereof, which cooperate with a plurality of circumferentially spaced fins or ribs on the needle holder.

Thus, when the user is prepared to use the assembly, the needle shield is removed from the needle, the assembly is used, and thereafter, the assembly must be discarded so that there is no contamination by the used needle. At this point in time, however, it is sometimes not feasible to discard a used blood collection assembly, for example, in the usual manner by destroying the needle in a needle destroyer arranged for that purpose. Nevertheless, it is important to avoid a reuse of the needle or the contamination of a user's skin subsequently with any contamination which may be contained on the needle or on the assembly. For this reason, the user is likely to insert the needle back into the shield so that no one is subjected to the needle point after its use.

It is difficult, however, in situations where blood has been collected from a patient to be able to insert precisely the needle point into the needle shield so that the shield may be replaced for covering and protecting the needle from subsequent contamination. It may be, for example, that the user is attempting to make further collections of separate portions or samples of blood, or it may be that the patient needs immediate attention. It is important in instances of this kind, that the needle shield may be readily replaced over the used needle so that the assembly may be rapidly laid aside without fear of contamination or reuse. It is this aspect of such an assembly that this invention is specifically directed to.

That is, this invention is directed to a needle shield with a radially positioned guidance opening which enables the user to readily and easily insert the point of the used needle into the open end of the needle shield. In other words, the user may utilize the combination of the open end of the needle shield together with the radial slot for guiding the point readily into the shield for replacing the shield over the needle assembly.

Further objects and advantages of the present invention, together with the organization and manner of operation thereof, will become apparent from the following detailed description of the invention when taken in conjunction with the accompanying drawings.

DESCRIPTION OF THE DRAWINGS

The single FIGURE is a longitudinal side view of apparatus, partly in section, showing a partial view of a blood collection assembly with the needle thereof, and the cooperating shield therefor illustrating the invention.

DETAILED DESCRIPTION OF THE INVENTION

Referring to the drawing, a blood collection assembly is shown partly in section and generally designated 10, with the assembly having a hub 12, with a lower annular wall 20 defining a holder for receiving an evacuated tube in space 21. As will be appreciated, the collection assembly may include other arrangements, not shown, depending upon the subsequent use of the collected sample.

Hub 12 has a forward end 13 with a bore 18 therein which is arranged to receive a cannula 24 therein. In this arrangement, the bore 18 extends to space 21. Cannula 24 may be held in bore 18 by a suitable adhesive.

Cannula 24 has a lower point 14 extending into space 21 for piercing the plug of an evacuated blood receiving tube inserted into space 21. Generally, point 14 is covered by a pierceable elastic sleeve 16 which maintains point 14 sterile until it pierces the plug of an evacuated container. Sleeve 16 has a hub 17, in turn, which abuts the lower end of hub 12, as shown in the drawing.

Forward end 13 of the housing also includes a plurality of circumferentially spaced ribs 22 surrounding the outwardly extending needle 24. A needle shield assembly 30 is arranged to cover the outwardly extending needle 24, and includes mating internal ribs or grooves within. The mating ribs between the needle shield and the needle housing allow the user to facilitate the insertion into or removal of the needle from the needle shield 30, as well as for maintaining the shield on the needle housing. The needle shield assembly 30, includes a forward body portion 32 adjacent to the opening or open end 38 of the shield assembly 30. As stated above, the body portion 32 includes a plurality of circumferentially spaced grooves 22a for cooperating with the ribs 22 on the needle assembly housing. The needle shield assembly includes an extended smaller diameter longitudinally extending portion 34 for receiving the extent of the needle 24 therein. Portion 34 of needle assembly 30 includes, of course, the closed end 40 of the needle shield.

In accordance with this invention, a radial opening 36 is provided adjacent the open end 38 of the needle shield assembly 30. With this arrangement, the radial opening 36 cooperates with the opening 38 at the end of the needle shield assembly 30 for enabling the user to rapidly guide the point 25 into the needle shield assembly 30 so as to reduce to a minimum any contamination of the user of the assembly 10 from the used needle 24.

Thus, as will be appreciated from the above discussion, a needle assembly is provided with a cooperating needle shield which may be easily and readily guided for replacement over the used needle point 25 once the assembly has been used. Moreover, as will be appreciated by practitioners-in-the-art, the needle shield assembly 30 may be readily mass produced in a variety of different materials, including several different thermoplastics by mass production techniques.

While the methods and forms of apparatus described constitute preferred embodiments of the invention, it is to be understood that the invention is not limited to these precise methods and forms of apparatus, and that changes may be made therein without departing from the scope of the invention which is defined in the appended claims. For example, although only one radial guidance opening 36 is shown in the needle assembly as described herein, it will be appreciated that diametrically opposed radial guidance openings may be utilized for a further easy reinsertion of a needle into the needle shield once the needle is used. Indeed, more than two such radial openings may be utilized, for the convenience of the user.

What is claimed is:

1. A needle shield for a needle holding assembly, characterized by
   (a) a longitudinally extending housing defining an elongated chamber therein;
   (b) said housing having a closed end and an open end;
   (c) at least one radial slot in said housing extending from said open end to a point spaced from said open end; and
   (d) said radial slot providing communication between said elongated chamber and outside said shield throughout the length of said slot.

2. The apparatus of claim 1, further characterized by
   (a) a plurality of circumferentially spaced grooves adjacent said open end for cooperating with a needle holding assembly.

3. A needle holding assembly, characterized by
   (a) a hub;
   (b) a needle extending from said hub;
   (c) a needle shield for said needle;
   (d) cooperating means on said needle shield and said hub for holding said needle shield on said hub;
   (e) said needle shield comprising
      (1) a longitudinal needle shield body defining an elongated chamber therein;
      (2) said elongated chamber for receiving said needle;
      (3) said needle shield body having an open end and a closed end;
      (4) at least one radial slot in said body extending from said open end to a point spaced from said open end; and
      (5) said radial slot providing communication between said elongated chamber and outside said shield throughout the length of said slot.

4. The apparatus of claim 3, further characterized by
   (a) said cooperating means includes a plurality of circumferentially spaced cooperating grooves in said elongated chamber adjacent the open end thereof; and
   (b) a plurality of cooperating ribs on said needle holding hub.

* * * * *